US009974716B2

(12) United States Patent
Catel et al.

(10) Patent No.: US 9,974,716 B2
(45) Date of Patent: May 22, 2018

(54) DENTAL PRIMER FORMULATION (71) Applicant: Ivoclar Vivadent AG, Schaan (LI)

(72) Inventors: Delphine Catel, Buchs SG (CH); Thorsten Bock, Feldkirch (AT); Ulrich Salz, Lindau (DE)

(73) Assignee: Ivoclar Vivadent AG, Schaan (LI)

(*) Notice: Subject to any disclaimer, the term of this patent is extended or adjusted under 35 U.S.C. 154(b) by 148 days.

(21) Appl. No.: 14/775,986

(22) PCT Filed: Feb. 19, 2014

(86) PCT No.: PCT/EP2014/000444
§ 371 (c)(1),
(2) Date: Sep. 14, 2015

(87) PCT Pub. No.: WO2014/139629
PCT Pub. Date: Sep. 18, 2014

(65) Prior Publication Data
US 2016/0022549 A1   Jan. 28, 2016

(30) Foreign Application Priority Data

Mar. 15, 2013  (EP) .................................. 13159634

(51) Int. Cl.
*A61K 6/00* (2006.01)
(52) U.S. Cl.
CPC .......... *A61K 6/0029* (2013.01); *A61K 6/0047* (2013.01)
(58) Field of Classification Search
CPC .......................... A61K 6/0029; A61K 6/0047
See application file for complete search history.

(56) References Cited

U.S. PATENT DOCUMENTS

| | | | | |
|---|---|---|---|---|
| 4,673,354 A | | 6/1987 | Culler | |
| 4,710,217 A | * | 12/1987 | Bailey | A61K 6/06 216/34 |
| 2010/0240796 A1 | * | 9/2010 | Bock | A61K 6/0026 523/118 |

FOREIGN PATENT DOCUMENTS

| | | |
|---|---|---|
| DE | 102005002750 A1 | 7/2006 |
| JP | 2593850 B2 | 3/1997 |
| JP | 2601254 B2 | 4/1997 |
| JP | 2010215624 A | 9/2010 |

OTHER PUBLICATIONS

Russell et al, "Shear Bond Strength of Resin Composite to Dicor Treated with 4-META", International Journal of Prosthodontics, vol. 7, No. 1, 1994, pp. 7-12.*
Alex, Gary, "Preparing Porcelain Surfaces for Optimal Bonding", Functional Esthetics & Restorative Dentistry, Series 2, No. 1, pp. 38-49.
Vohra, Rais et al., "Recurrent life-threatening ventricular dysrhythmias associated with acute hydrofluoric acid ingestion: Observations in one case and implications for mechanism of toxicity", Clinical Toxicology, 2008, vol. 46, pp. 79-84.
Barghi, Nasser, et al., "Effect of Leucite Content of Porcelain, Types of Etchant and the Etching Time on Porcelain-Composite Bond", Journal of Esthetic Restorative Dentistry, 2006, vol. 18, pp. 47-52.
Amaral, Paulo Roberto, et al., "Effect of Etching Time and Light Source on the Bond Strength of Metallic Brackets to Ceramic", Brazilian Dental Journal, 2011, vol. 22, pp. 245-248.
Nagayassu, Marcos Paulo, et al., "Effect of Surface Treatment on the Shear Bond Strength or a Resin-Based Cement to Porcelain", Brazilian Dental Journal, 2006, vol. 17, pp. 290-295.
Tylka, Daniel F., et al., "Comparison of acidulated phosphate fluoride gel and hydrofluoric acid etchants for porcelain-composite repair", School of Dental Medicine,1994, vol. 72, pp. 121-127.
Bona, Alvaro Della, "Microstructure, Composition, and Etching Topography of Dental Ceramics", The International Journal of Prosthodontics, 2002, vol. 15, pp. 159-167.
Bona, Alvaro Della, "Effect of Ceramic Surface Treatment on Tensile Bond Strength to a Resin Cement", The International Journal of Prosthodontics, 2002, vol. 15, pp. 248-253.
Cömlekolu, Erhan et al., "Preliminary Evaluation of Titanium Tetrafluoride as an Alternative Ceramic Etchant to Hydrofluoric Acid", Journal of Adhesive Dentistry, 2009, vol. 11, pp. 447-453.
Kern, Matthias et al., "Bonding to glass infiltrated alumina ceramic: Adhesive methods and their durability", The Journal of Prosthetic Dentistry, 1995, vol. 73(3), pp. 240-249.
Kern, M., et al., "A simple test arrangement for a comprehensive/ universal study of the glue compound during the examination of the axial force", Deutsche Zahnärztl. Z, 1993, vol. 48, pp. 769-772. (see English-language summary on last page of submitted reference).
Russell, David A., et al., "Shear Bond Strength of Resin Composite to Dicor Treated with 4-META", The International Journal of Prosthedontics, 1994, Series 7, No. 1, pp. 7-12.
Tsai, Yueh-Long, et al., "Influence of Glass-Ceramic Thickness on Hertzian and Bulk Fracture Mechanisms", The International Journal of Prosthedontics, 1998, vol. 11, No. 1, pp. 27-32.
McInnes-Ledoux, P.M., et al., "A Bond Strength Study of Luted Castable Ceramic Restorations", Journal of Dental Restorations, 1989, vol. 68(5), pp. 823-825.

(Continued)

*Primary Examiner* — C Melissa Koslow
(74) *Attorney, Agent, or Firm* — Ann M. Knab; Thad McMurray (57) ABSTRACT

Primer formulation which contains (1) at least one alkoxysilane monomer of the general formula $R^1{}_n Si(OR^2)_{4-n}$ (I), wherein $R^1$ stands for an organic residue which contains at least one ethylenically unsaturated, polymerizable group, $R^2$ stands for a $C_1$-$C_8$ alkylorganic residue and n is 1, 2 or 3, wherein the residues $R^1$ and $R^2$ can each be the same or different; (2) at least one polyhydrogen fluoride salt of the general formula $(R^9)^+(H_{x-1}F_x)^-{}_z$ (II), wherein $R^9$ stands for a metal cation from the series of the alkali, alkaline earth or transition metals or for an ammonium ion of the formula $(R^5)(R^6)(R^7)(R^8)N^+$, in which $R^5$ $R^6$ $R^7$ and $R^8$ each independently of each other stand for H or $C_1$ to $C_{12}$ alkyl, $C_3$ to $C_{12}$ alkenyl or $C_6$-$C_{12}$ aryl residues, wherein $R^5$, $R^6$, $R^7$ and $R^8$ can be the same or different, and wherein two of these residues can be bound together to form a heterocycle together with the nitrogen atom and wherein three of the residues and the nitrogen atom can together form a pyridinium ion, x is an integer from 2 to 5, preferably 2 to 4, in particular 3, z corresponds to the valence of the cationic residue $R^9$, (3) organic solvent, and (4) water.

27 Claims, 4 Drawing Sheets

(56) References Cited

OTHER PUBLICATIONS

Queiroz, J.R.C., et al., "Influence of acid-etching and ceramic primers on the repair of a glass ceramic", General Dentistry, Mar./Apr. 2012, vol. 60(2), pp. 79-85.
Wikipedia, "Residue", https://en.wikipedia.org/wiki/Residue_(chemistry), Nov. 15, 2016.
Bailey, L. F., et al., "DICOR Surface Treatments for Enhanced Bonding," Journal of Dental Research, vol. 67, pp. 925-931, Jun. 1988.
Yanagida, et al., "Effects of a metal etchant and two primers on resin bonding durability to titanium," European Journal of Oral Science, vol. 112, No. 1, pp. 95-100, 2004.
Matinlinna, J., et al., "Experimental Novel Silane System in Adhesion Promotion between Dental Resin and Pretreated Titanium. Part II: Effect of Long-Term Water Storage," Silicon, vol. 2., No. 2., pp. 79-85, Tab 1, 2; 2010.

\* cited by examiner

DENTAL PRIMER FORMULATION

CROSS-REFERENCE TO RELATED APPLICATIONS

This application is a National Stage application of International Patent Application No. PCT/EP2014/000444 filed on Feb. 19, 2014, which claims priority to European Patent Application No. 13159634 filed on Mar. 15, 2013, the disclosures of which are incorporated herein by reference in their entirety.

The present invention relates to dental primer formulations which are suitable in particular for the treatment of ceramic surfaces.

In dental technology, the distinction is made between ceramic and metallic restoration materials, the ceramic materials being further subdivided into silicate ceramics such as for example feldspar, quartz, leucite-based ceramics and glass ceramics, and lithium disilicate-based ceramics ("silicates"), and non-silicate ceramics, such as for example yttrium-stabilized zirconium oxide, aluminium oxide and glass-infiltrated aluminium oxide (e.g. In-CERAM Alumina, Vita, Germany) ("oxide ceramics"). Among the metals, the distinction is made between base metals such as for example chromium, nickel, molybdenum, titanium and alloys thereof ("BM"), and noble metals such as for example gold, platinum, palladium, silver and alloys thereof ("NM").

In the production of dental restorations, it is often necessary to bind these materials durably to one another or to the natural tooth substance. Generallly, polymerizable composites and cements are used for this. According to the state of the art, the bond is produced in a two-step process. In the first step, the surface of the restoration materials is roughened by wet-chemical or mechanical-abrasive methods. The roughening serves to create a microretentive surface structure and to increase the surface area. To those skilled in the art, both aspects are known to be important for the provision of a durably load-bearing bond.

The method usual in dental technology for the wet-chemical erosion ("etching") of silicates mainly uses aqueous hydrofluoric acid solutions. In spite of the beneficial effects as regards the bonding action, hydrofluoric acid (HF) is disadvantageous as an etching agent for various reasons. Firstly, the use of HF in the dental-medical application is associated with a hazard potential because of its toxicity (G. Alex, Functional Esthetics & Restoration Dentistry, Series 2, Number 1, 38-49; Vohra et al., Clinical Toxicology (2008) 46, 79-84).

Moreover, apart from their disadvantageous toxicity, HF solutions can structurally damage the ceramic through excessively long exposure ("over-etching"), which worsens both the mechanical properties of the ceramic and the bond to the fixing cement (Barghi et al., Journal of Esthetic Restoration Dentistry (2006) 18, 47-52; Amaral et al., Brazilian Dental Journal (2011) 22, 245-248; Nagayassu et al., Brazilian Dental Journal (2006) 17, 290-295). The authors of these articles come to the conclusion that the HF concentration and HF exposure time must be carefully adapted to the silicate ceramic to be etched, in order to create a retentive surface without structurally damaging the ceramic or weakening the bond.

In order to avoid these disadvantages, efforts have been made in the past to replace hydrofluoric acid with less toxic alternative substances. Tylka et al, The Journal of Restoration Dentistry (1994) 72, 121-127, propose the use of acidic fluorophosphate solutions for intraoral use. Della Bona et al., Int J Prosthodont (2002) 15, 159-167, compare ammonium bifluoride (ABF), hydrofluoric acid and acidic fluorophosphate solutions. HF yielded the clearest etching pattern, and it could be shown that HF results in a significantly greater adhesive strength than the other materials (Della Bona, Int J Prosthodont (2002) 15, 248-253). Cömlekoglu et al., Journal of Adhesive Dentistry (2009), 11, 447-453, found that the treatment of ceramic surfaces with aqueous titanium tetrafluoride ($TiF_4$) solution causes the formation of surface $TiO_2$ layers which should ensure good adhesion values. However, the authors point out that the adhesion of the $TiO_2$ layers to the ceramic can be impaired by aging. The said HF-free methods have not hitherto been satisfactory.

It is common to all etching methods that for the preparation of an adhesive fixation, the silicate ceramic workpieces are contacted with the etching solution and after a certain exposure time the solution is rinsed off with water. Next, the silicate surface has to be dried with compressed air before further process steps can be performed. Since in the reaction between silicate and etching solution the amorphous components of the silicates are preferably converted to soluble hexafluorosilicate and the crystalline components remain, a bond-promoting rough (microretentive) surface structure is formed.

The most common mechanical-abrasive method is sandblasting, wherein abrasive particles accelerated with compressed air are directed against the surface to be treated. Through the high kinetic energy of the particles, a microretentive structure is attained. Where the use of sandblasting can lead to adverse effects on the patient (e.g. intraorally) or suitable instruments are not available, the roughening can also be introduced for example by means of rotating instruments. For optical reasons, sandblasting is suitable only to a limited extent for visible regions of dental restorations.

In the second step, the roughened restoration surface is provided with polymerizable functionality ("priming") through an adhesion promoter ("primer"). The primer contains monomers which on the one hand can bind via reactive groups onto the surface of the restoration and on the other hand have polymerizable groups which enable copolymerization with further monomers. For example, silanes can react with silicate surfaces with the formation of covalent Si—O—Si linkages, while phosphates form zirconium (oxo-phosphates) with zirconium oxide. The polymerizable groups can at a later time be copolymerized by suitable methods with the composite or cement used for fixing the restoration. In this manner, a durable bond between restoration and composite, characterized by covalent or ionic bonds, can be created.

Previously known primers for the adhesive fixing of dental restoration materials are not capable of etching silicates and are suitable only for surface functionalization. However, an adhesive bond introduced through silanization alone is markedly weaker than that achieved by a combination of HF etching and silanization (Queiroz et al, Gen Dent. (2012), 60(2), 9-85). Hence according to the current state of the art, for a clinically significant bond to silicates, it is essential to effect prior roughening of the surface and the subsequent silanization of the roughened surface in separate process steps. Typical primers of the above type are described in the following documents.

EP 0 224 319 A1 describes a primer composition for adhesion improvement on various ceramic materials, which contains a silane hydrolyzable to an organofunctional silanol.

The subject of JP 2601254 B2 is a dental primer for ceramics and metal which contains the combination of an organofunctional silane with specific (meth)acryloyl-functional phosphoric acid monoesters.

JP 2593850 B2 describes an adhesive dental composition which inter alia contains an organofunctional silane and an acidic organic phosphorus compound with a radically polymerizable double bond. The composition is supposed to enable binding both to metals and to ceramic.

In DE 10 2005 002 750 A1, a primer for dental noble metal alloys is disclosed, which contains special disulphides substituted with polymerizable groups.

EP 2 229 930 A1 discloses a dental adhesion promoter composition which is suitable for different metals and ceramics. As well as an alkoxysilane, the compositions contain a phosphoric acid ester monomer, a sulphur-containing monomer and solvent.

Primers which would be suitable for simultaneous etching and priming of silicate restoration surfaces are not described in the state of the art.

The separate etching and priming of a silicate ceramic restoration before the adhesive cementing requires many process steps from the operator, namely application of an etching gel onto the silicate ceramic, allowing it to act, rinsing off of the etching gel, drying of the surface, application of a primer and allowing it to act and finally blowing off of the primer with an air blower. Hence this is a very time- and labour-intensive process.

SUMMARY OF THE INVENTION

The object of the invention is to provide a dental primer which does not display the aforesaid disadvantages. In particular, without prior etching or roughening the primer should be capable of application directly onto the surface to be treated and ensure a reliable bond under oral conditions. The primer should have low toxicity and high stability.

DETAILED DESCRIPTION

According to the invention, this object is achieved by a primer formulation which contains the following components:

(1) at least one alkoxysilane monomer of the general formula (I)

$$R^1_n Si(OR^2)_{4-n} \qquad (I),$$

in which
R$^1$ stands for an organic residue which contains at least one polymerizable group,
R$^2$ stands for H or a $C_1$ to $C_8$ alkyl residue, preferably $C_1$ to $C_4$ alkyl residue and
n is 1, 2 or 3,
wherein the residues R$^1$ and R$^2$ can each be the same or different;

(2) at least one polyhydrogen fluoride salt of the general formula (II)

$$(R^9)+(H_{x-1}F_x)^-_z \qquad (II),$$

in which
R$^9$ stands for a metal cation from the series of the alkali, alkaline earth or transition metals or for an ammonium ion of the formula $(R^5)(R^6)(R^7)(R^8)N^+$, in which R$^5$, R$^6$, R$^7$ and R$^8$ each independently of each other stand for H or $C_1$ to $C_{26}$ alkyl, $C_3$ to $C_{26}$ alkenyl or $C_6$-$C_{26}$ aryl residues, preferably $C_1$ to $C_{12}$ alkyl, $C_3$ to $C_{12}$ alkenyl or $C_6$-$C_{12}$ aryl residues, wherein R$^5$, R$^6$, R$^7$ and R$^8$ can be the same or different, and wherein two of these residues can be bound together to form a heterocycle together with the nitrogen atom, and wherein three of the residues and the nitrogen atom can together form a pyridinium ion,
x is an integer from 2 to 5, preferably 2 to 4, in particular 3, z corresponds to the valence of the cationic residue R$^9$,
(3) organic solvent, and
(4) water.

Preferred alkoxysilanes of Formula (I) are those compounds in which the variables have the following meanings:
R$^1$=a residue with the following formula:

in which
R$^{1a}$=H or phenyl, preferably H;
R$^{1b}$=H or methyl, preferably methyl;
R$^{1c}$ is absent or is $C_1$-$C_{16}$ alkyl, preferably $C_1$-$C_3$ alkyl;
X is absent or is —CO—O— or —CO—NH—, preferably —CO—O— or —CO—NH—, wherein X is absent when R$^{1c}$ is absent;
R$^2$=H or $C_1$ to $C_2$ alkyl and
n=1 or 2,
wherein the residues R$^1$ and R$^2$ can each be the same or different and wherein several residues R$^1$ or R$^2$ are preferably the same.

Preferred polyhydrogen fluorides of Formula (II) are those compounds in which the variables have the following meanings:

x=an integer from 2 to 4, preferably 3,
z=1,
$R^9$=an ammonium ion of the formula $(R^5)(R^6)(R^7)(R^8)N^+$, in which $R^5$, $R^6$, $R^7$ and $R^8$ independently of each other mean H, $C_1$-$C_4$ alkyl, wherein $R^5$, $R^6$, $R^7$ and $R^8$ are preferably the same, and preferably $R^5$=$R^6$=$R^7$=$R^8$=butyl, in particular n-butyl.

The aforesaid preferred meanings of the variables can be selected independently of each other, wherein those compositions which contain preferred compounds of Formulae (I) and (II) are particularly preferred.

The primer formulations according to the invention are characterized by their ability to etch surfaces of silicate ceramics and simultaneously to functionalize them with polymerizable groups. They have self-etching properties and thus combine the functions of conventional etching agents and primers in one composition. This means a considerable saving of labour for the user, since the separate etching and functionalization of the surfaces is eliminated and replaced by a joint process step. In addition, the primer formulations according to the invention are characterized by low toxicity, and they are thus also suitable for intraoral use. Apart from this, the primers according to the invention exhibit high stability. No clouding due to polycondensation of the silanes occurs.

The surfaces treated with the primers according to the invention enter into a stable adhesive bond with polymerizable, radically curing dental materials, in particular with dental composites and radically polymerizable cements, which is comparable to the conventional method of separate etching and priming. The bonding action is not significantly reduced by thermocycling stress, which is an essential criterion for an adhesive strength usable in dentistry. Dental composites are mixtures of inorganic fillers with polymerizable organic monomers. Polymerizable cements differ from the composites in that they contain less filler or none.

The primers are preferably in the form of homogeneous solutions. They are particularly suitable for dental-medical applications which require durable bonding of polymerizable mixtures with prefabricated restorations based on silicate ceramic. The formulations according to the invention, in contrast to the state of the art, enable wet-chemical etching and the functionalization of silicate surfaces in one process step. For this, two reactions, which are usually performed successively, must proceed in parallel. It could not be expected that this would automatically be the case. It was rather to be assumed that through the etching of the surface, i.e. the chemical removal of surface regions, already introduced functional groups would be detached again or else that surface-bonded functional groups would impede the access of the etching agent to the surface and thus the etching process.

The alkoxysilane monomer of Formula (I), as well as the hydrolysablealkoxy group —$OR^2$ contains at least one residue $R^1$ which contains at least one, preferably exactly one polymerizable group. Typically, this is a radically polymerizable group. Preferably the alkoxysilane has one or two $R^1$ residues. Preferably $R^1$ contains an ethylenically unsaturated double bond. For example $R^1$ can contain a (meth)acryloyl, (meth)acryloyloxy group ($H_2C$=$C(R^{15})$—CO—O— with $R^{15}$=$CH_3$ or H), a (meth)acryloyl-amino group ($H_2C$=C($R^{16}$)—CO—NH— with $R^{16}$=$CH_3$ or H), a vinyl, allyl or styryl group, wherein the said groups can be unsubstituted or substituted with suitable substituents. Unsubstituted groups are preferred. Preferred residues $R^1$ include (meth)acryloyloxyalkyl, preferably (meth)acryloyloxy-$C_2$-$C_{16}$ alkyl, particularly preferably (meth)acryloyloxypropyl; (meth)acryloylaminoalkyl, preferably (meth)acryloyl-amino-$C_2$-$C_{16}$ alkyl, particularly preferably (meth)acryloylaminopropyl; vinyl; allyl and styryl.

Suitable substituents are aryl, alkylaryl, heteroalkyl, heteroaryl, heteroalkylaryl, urethane, halogen, isocyanate, ureide, and/or imidazolinyl groups and also aryl, alkylaryl, heteroalkyl, heteroaryl, and/or heteroalkylaryl residues, which are substituted with urethane, halogen, isocyanate, ureide, imidazolinyl groups, acryloyloxy and/or methacryloyloxy groups, in particular with urethane, halogen, isocyanate, ureide, and/or imidazolinyl groups.

The alkyl residue $R^2$ of the alkoxy group in Formula (I) contains 1 to 8 C atoms and is branched or preferably straight-chain. Preferably $R^2$ is a methyl, ethyl, n- or i-$C_3$-$C_8$ residue, particularly preferably methyl or ethyl.

Particularly suitable alkoxysilane monomers (I) for the present invention are 3-meth-acryloyloxypropyltrimethoxysilane (MPTMS), 3-methacryloyloxypropyltriethoxysilane (MPTES), di(3-methacryloyloxypropyl)dimethoxysilane (DPDMS) and 3-methacryloylamidopropyltrimethoxysilane (MAPTMS). The most preferable silanes are 3-meth-acryloyloxypropyltrimethoxysilane and 3-methacryloylamidopropyltrimethoxysilane.

The alkoxysilane monomer (I) is typically present in the primer formulation according to the invention in a proportion of from 0.05 to 25.0 wt. %, preferably 0.2 to 10.0 wt. % and particularly preferably 0.5 to 5.0 wt. %, each based on the total weight of the composition.

In addition to the alkoxysilane of Formula (I), the primer according to the invention can additionally contain a further alkoxysilane of the general formula (Ia), $$(R^{13}O)_3SiR^{12}Si(OR^{13})_3 \qquad (Ia),$$

wherein
$R^{12}$ stands for $C_1$-$C_{12}$ alkylene, $C_1$-$C_{12}$ heteroalkylene, e.g. oligoethylene glycol, or $C_6$-$C_{12}$ arylene, e.g. phenylene, and
$R^{13}$ independently in each case stands for H or $C_1$ to $C_8$ alkyl,
wherein the residues $R^{13}$ can each be the same or different.

Preferred alkoxysilanes of Formula (Ia) are those compounds in which the variables have the following meanings:
$R^{12}$=$C_1$ to $C_6$ alkylene, preferably $C_2$-$C_6$ alkylene, which can contain one or more, preferably one, O atom(s), one or more, preferably one, S atom(s), or preferably one or more, preferably one, NH group(s), or phenylene,
$R^{13}$=H, $C_1$-$C_8$ alkyl, preferably n- or i-$C_1$-$C_8$ alkyl, particularly preferably methyl or ethyl, wherein the residues $R^{13}$ can be different or preferably the same.

Residues with no hetero atoms are preferred.

The bis(alkoxysilane) of Formula (Ia), in addition to the bridging group —$R^{12}$— contains three hydrolyzable alkoxy groups —$OR^{13}$ per Si atom. The bis(alkoxysilanes) (Ia) are always used as a mixture with the alkoxysilane monomer (I). The alkyl residue $R^{13}$ of the alkoxy group in Formula (Ia) contains 1 to 8 C atoms and is preferably an n- or i-$C_1$-$C_8$ residue, particularly preferably methyl or ethyl.

Particularly suitable bis(alkoxysilanes) (Ia) for the present invention are bis(triethoxysilyl)ethane, bis(triethoxysilylethyl)benzene and N,N-bis[3-(trimethoxy-silyl)propyl]amine. The most preferable bis(alkoxysilane) is bis(triethoxysilyl)ethane.

The bis(alkoxysilane) (Ia), if applicable, is preferably present in the primer formulation according to the invention in a quantity of from 0.005 to 2.50 wt. %, preferably 0.02 to 1.0 wt. % and particularly preferably 0.05 to 0.5 wt. %, each based on the total weight of the composition.

The polyhydrogen fluoride-containing salt of the general formula (II) is characterized by good solubility in the solvent mixture used. Those compounds are preferable which are soluble in the concentrations stated below in the solvent used. $R^5$, $R^6$, $R^7$ and $R^8$ are part of an ammonium ion and are preferably the same or independently of each other H, n- or i-alkane or alkenyl with a chain length of $C_1$ to $C_{26}$, preferably $C_{3\text{-}12}$. $R^5$, $R^6$, $R^7$ and $R^8$ can also be bound together as part of a cyclic ammonium compound. Preferred residues $R^5$, $R^6$, $R^7$ and $R^8$ are H, $C_1$ to $C_4$ n- or i-alkanes, wherein $R^5$, $R^6$, $R^7$ and $R^8$ are the same. Particularly preferably $R^5=R^6=R^7=R^8$=butyl, in particular n-butyl. The polyhydrogen fluoride anion contained in Formula (II) is characterized by x=2-5, preferably 2-4, and x=3 is particularly preferred.

The groups $R^5$ to $R^8$ can be substituted or preferably unsubstituted. Preferred substituents are halogen, in particular chlorine and bromine, and aromatic and heteroaromatic groups, preferably phenyl and pyridinyl. If applicable, the groups $R^5$ to $R^8$ are preferably substituted with 1 to 12, particularly preferably 1 to 6 and in particular 1 to 4 halogen atoms or 1 to 4 aromatic or heteroaromatic units.

In a further embodiment, ($R^9$) is a metal cation. These are biologically compatible metal cations, preferably sodium or potassium.

The polyhydrogen fluoride-containing salt (II) is typically present in the primer composition according to the invention in a quantity of from 1 to 25.0 wt. %, preferably 2.0 to 15.0 wt. % and particularly preferably 5.0 to 10.0 wt. %, each based on the total weight of the composition.

Component (3) of the primer formulation according to the invention is an organic solvent or a solvent mixture consisting of physiologically compatible solvents. Suitable solvents are for example alcohols, ketones and esters, wherein methanol, ethanol, n-propanol, i-propanol, t-butanol, ethyl acetate, acetone, methyl ethyl ketone and mixtures thereof are preferred. Particularly preferred is ethanol.

Typically the primer formulation contains 25 to 98.5 wt. %, preferably 35 to 75 wt. % and particularly preferably 45 to 55 wt. % organic solvent, each based on the total weight of the composition.

Component (4) is the water necessary for improvement of the etching action of the polyhydrogen fluoride salt. Typically the primer formulation contains 25 to 98.5 wt. %, preferably 35 to 75 wt. % and particularly preferably 40 to 75 wt. % water, each based on the total weight of the composition.

The primers according to the invention are particularly suitable for the treatment of the surfaces of dental restorations with silicate ceramic surfaces. The simultaneous etching and priming of silicate ceramics with the self-etching primer formulation according to the invention requires only four process steps, (1) the application of the primer onto the surface, (2) allowing the primer to act, (3) the rinsing off of the self-etching primer with water or a suitable solvent and (4) the drying of the surface. The use of a self-etching primer thus reduces the number of process steps necessary for the preparation of silicate ceramics and thus renders a faster and less error-prone procedure possible.

The primer according to the invention preferably contains no free HF, i.e. it succeeds without admixture or in situ formation of free hydrofluoric acid. This increases the occupational safety as regards occurring toxic or tissue-destructive effects in the event of unintended contact.

In addition to the silane of Formula (I) and the polyhydrogen fluoride salt (II), the primer according to the invention can contain as component (5) a phosphoric or pyrophosphoric acid ester monomer of Formula (III):

in which
$R^3$ stands for an organic residue which contains at least one ethylenically unsaturated, polymerizable group,
$R^4$ stands for H, $SiR_3$, $P(=O)(OR^{14})_2$ or $C_1$ to $C_{16}$ alkyl, preferably H, wherein $R^{14}$ stands for H, $SiR'_3$ or $C_1$ to $C_{16}$ alkyl, preferably H, and wherein R and R' independently of each other are each $C_1$ to $C_4$ alkyl and in particular methyl, and
m is 1 or 2,
wherein several residues $R^3$ and $R^4$ can each be the same or different.

Preferred compounds of Formula (III) are those compounds in which the variables have the following meanings:
$R^3$=a residue with the following formula:

in which
$R^{3a}$=H or phenyl, preferably H;
$R^{3b}$=H or methyl, preferably methyl;
$R^{3c}$ is absent or is $C_1$-$C_{16}$ alkyl, preferably $C_2$-$C_3$ alkyl;
X is absent or is —CO—O— or —CO—NH—, preferably —CO—O— or —CO—NH—, wherein X is absent when $R^{3c}$ is absent;
r=1 or 2;
$R^4$=methyl, ethyl, preferably H;
m=1,
wherein the residues $R^4$ are different or preferably the same.

Through the addition of the compound (III), the adhesion of the primer to oxide ceramics and base metals is improved. In this manner, the application spectrum of the primer according to the invention is extended to such materials. This enables the use of the primer for improving the bonding action between a radically curing dental material and a multitude of other dental restoration materials. As a result, compared to substrate-specific primers, in clinical use the risk of confusion and the risk of clinical failure can be reduced. A particular advantage of such universally usable primers is that they can be used in restorations which contain different materials. This is for example often the case with the repair of fractured ceramic veneers where several substrates are present directly adjacent to one another in a narrow space.

The phosphoric acid ester monomer of the general formula (III) contains at least one residue $R^3$ which contains at least one, preferably one or two polymerizable groups. Typically these are radically polymerizable group(s). The phosphoric acid ester preferably has exactly one $R^3$ residue.

In the presence of water, pyrophosphates ($R^4$=$P(=O)$ $(OR^{14})_2$) are hydrolyzed in the course of time to phosphates of Formula (III).

Preferably $R^3$ in Formula (III) contains at least one ethylenically unsaturated double bond. For example, $R^3$ can contain at least one (meth)acryloyloxy group, one (meth) acryloylamino group, one vinyl, allyl or styryl group or a combination thereof. Preferred residues $R^3$ include (meth) acryloyloxyalkyl, preferably (meth)acryloyloxy-$C_2$-$C_{16}$ alkyl, particularly preferably (meth)acryloyloxy-$C_4$-$C_{14}$ alkyl, quite particularly preferably (meth)acryloyloxy-$C_6$-$C_{10}$ alkyl; di(meth)acryloyloxyalkyl, preferably di(meth)acryloyloxy-$C_2$-$C_{16}$ alkyl, particularly preferably di(meth)acryloyloxy-$C_2$-$C_{10}$ alkyl, quite particularly preferably di(meth)acryloyloxyisopropyl; (meth)acryloylaminoalkyl, preferably (meth)acryloylamino-$C_2$-$C_{16}$ alkyl, particularly preferably (meth)acryloylamino-$C_4$-$C_{14}$ alkyl, and quite particularly preferably (meth)acryloyl-amino-$C_6$-$C_{10}$ alkyl.

The $R^4$ residue is preferably selected from H, silyl, preferably $SiMe_3$, and $C_1$ to $C_{16}$ alkyl, wherein the alkyl residue can be branched or preferably straight-chain, preferably $R^4$ is H, methyl, ethyl or an n- or i-$C_3$-$C_{16}$ residue. In a particularly preferred embodiment, $R^4$ is H, while the dihydrogen phosphates (phosphoric acid monoesters) are the most preferred phosphoric acid ester monomers.

Phosphoric acid ester monomers (III) particularly suitable for the present invention are 1-methacryloyloxydecane-10-phosphate (MDP), 1-methacryloyloxyhexane-6-phosphate (MHP), 1-methacryloylamidodecane-10-phosphate (MADP), 1-acryloyl-amidohexane-6-phosphate (AAHP), 1,3-dimethacryloyloxypropane 2-phosphate (DMPP) and 1,3-dimethacryloylamidopropane 2-phosphate (DMAPP). The most preferred phosphoric acid ester monomer is 1-methacryloyloxydecane-10-phosphate.

The phosphoric acid ester monomer (III), if applicable, is preferably used in a quantity of from 0.05 to 25.0 wt. %, particularly preferably 0.2 to 10.0 wt. % and quite particularly preferably 0.5 to 5.0 wt. %, each based on the total weight of the composition.

Instead of or preferably in addition to the phosphoric or pyrophosphoric acid ester monomer of Formula (III), the primer according to the invention can contain one or more phosphonic acid or polyphosphonic acid monomers of the general formula (IIIa):

$$R^{11}[P(=O)(OR^{10})_2]_n \qquad (IIIa)$$

in which
$R^{11}$ stands for an organic residue which contains at least one ethylenically unsaturated, polymerizable group,
$R^{10}$ stands for a residue selected from H, $SiR''_3$ or $C_1$ to $C_{16}$ alkyl, wherein R" is $C_1$ to $C_4$ alkyl, preferably methyl,
n is 1, 2, 3 or 4, preferably 1 or 2 and in particular 1, wherein the residues $R^{10}$ can each be the same or different.

Preferred compounds of Formula (IIIa) are those compounds in which the variables have the following meanings:
$R^{11}$=a residue of the general formula in which
$R^{11a}$=H or phenyl, preferably H;
$R^{11b}$=H or methyl, preferably methyl;
$R^{11c}$ is absent or is $C_1$-$C_{16}$ alkyl, preferably $C_2$-$C_3$ alkyl;
X is absent or is —CO—O— or —CO—NH—, preferably —CO—O— or —CO—NH—, wherein X is absent when $R^{11c}$ is absent;
s=1 or 2;
$R_{10}$=methyl, ethyl, preferably H;
m'=1 or 2, preferably 1,
p=1, wherein the residues $R^{10}$ are different or preferably the same.

The phosphonic acid monomer of the general formula (IIIa) contains at least one residue $R^{11}$ which contains at least one, preferably one or two polymerizable groups. Typically, these are radically polymerizable group(s). The phosphonic acid (IIIa) preferably has exactly one $R^{11}$ residue.

Preferably $R^{11}$ in Formula (IIIa) contains at least one ethylenically unsaturated double bond. For example, $R^3$ can contain at least one (meth)acryloyloxy group, one (meth)acryloylamino group, one vinyl, allyl or styryl group or a combination thereof. Preferred residues $R^3$ include (meth)acryloyloxyalkyl, preferably (meth)acryloyloxy-$C_2$-$C_{16}$ alkyl, particularly preferably (meth)acryloyloxy-$C_4$-$C_{14}$ alkyl, quite particularly preferably (meth)acryloyloxy-$C_6$-$C_{10}$ alkyl; di(meth)acryloyloxyalkyl, preferably di(meth)acryloyloxy-$C_2$-$C_{16}$ alkyl, particularly preferably di(meth)acryloyloxy-$C_2$-$C_{10}$ alkyl, particularly preferably di(meth)acryloyloxyisopropyl; (meth)acryloylaminoalkyl, preferably (meth)acryloylamino-$C_2$-$C_{16}$ alkyl, particularly preferably (meth)acryloyl-amino-$C_4$-$C_{14}$ alkyl, quite particularly preferably (meth)acryloylamino-$C_6$-$C_{10}$ alkyl.

The $R^{10}$ residue is preferably selected from H, silyl, preferably $SiMe_3$, and $C_1$ to $C_{16}$ alkyl, wherein the alkyl residue can be branched or preferably straight-chain, $R^{10}$ is preferably H, methyl, ethyl or an n- or i-$C_3$-$C_{16}$ residue. In a particularly preferred embodiment, $R^{10}$ equals H, wherein the dihydrogen phosphonates (phosphonic diacids) are the most preferred phosphonic acid monomers Phosphonic acid monomers (IIIa) particularly suitable for the present invention are 1-methacryloyloxydecane-10-phosphonate, 9-methacryloyloxynonylphosphonic acid and ethyl 2-[4-(dihydroxyphosphoryl)-2-oxabutyl]-acrylate phosphonate. The most preferred phosphonic acid monomer is 9-methacryloyloxynonylphosphonic acid.

The phosphonic acid monomer (IIIa), if applicable, is preferably used in a quantity of from 0.05 to 25.0 wt. %, particularly preferably 0.2 to 10.0 wt. % and quite particularly preferably 0.5 to 5.0 wt. %, each based on the total weight of the composition.

The formulae shown above comprise only those compounds which are compatible with the chemical doctrine of equivalence. According to the invention all those compounds are preferred in which all variables have one of the preferred and in particular one of the particularly preferred meanings. Likewise, those primers are preferred which contain a combination of preferred or particularly preferred components, wherein the primer formulation according to the invention can in each case contain one of the said components or a mixture of several substances of the type in question.

Furthermore, the primer formulation according to the invention can contain additional additives (6), such as wetting agents, detergents, such as for example nonionic, anionic and/or cationic surfactants, preferably nonionic and cationic surfactants, antifoaming agents, stabilizers and other additives such as antimicrobial additives, fragrances, colorants and preservatives. The primer formulation according to the invention can contain polymeric thickeners, e.g. suitable soluble polyvinyl compounds, polymethacrylates, polyacrylates, polyethers, polyamines, polysilicates and polysaccharides, and thixotropic agents and rheology modifiers.

Particularly preferred are compositions which contain thickeners, colorant(s), radical stabilizer(s) and/or surfactant as additives.

Preferred additives are nonionic thickeners and colorants in proportions of 0.001-5 wt. % in each case, wherein the total content of additive (6) in the formulation lies in the range of from 0.001 to 10 wt. %.

According to a preferred embodiment, the primer formulation of the present invention contains:
(1) 0.05 to 25.0 wt. %, preferably 0.2 to 10.0 wt. % and particularly preferably 0.5 to 5.0 wt. % of alkoxysilane monomer (I) and optionally 0.005 to 2.5 wt. %, preferably 0.02 to 1.0 wt. % and particularly preferably 0.05 to 0.5 wt. % of the alkoxysilane (Ia);
(2) 1.0 to 25.0 wt. %, preferably 2.0 to 15.0 wt. % and particularly preferably 5.0 to 10.0 wt. % of polyhydrogen fluoride salt (II);
(3) 25 to 98.5 wt. %, preferably 35 to 75 wt. % and particularly preferably 45 to 55 wt. % of organic solvent;
(4) 25 to 98.5 wt. %, preferably 35 to 75 wt. % and particularly preferably 40 to 75 wt. % water;
(5) optionally 0.05 to 25.0 wt. %, preferably 0.2 to 10.0 wt. % and particularly preferably 0.5 to 5.0 wt. % of phosphoric acid ester monomer (III) and optionally 0.05 to 25.0 wt. %, preferably 0.2 to 10.0 wt. % and particularly preferably 0.5 to 5.0 wt. % of phosphonic acid monomer (IIIa);
(6) optionally 0.001 to 10%, preferably 0.1 to 7.5%, particularly preferably 1.0 to 5% of additives
each based on the total weight of the composition.

Quite particularly preferred according to the invention are the primer formulations A, B and C, which contain the following components:
(A) a combination of (I) 3-methacryloxypropyltrimethoxysilane, (II) tetrabutylammonium dihydrogen trifluoride and (III) 1-methacryloyloxydecane-10-phosphate;
(B) a combination of (I) (3-trimethoxysilylpropyl)methacrylamide; (II) tetrabutylammonium hydrogen difluoride and (III) 1-methacryloylamidodecane-10-phosphate;
(C) a combination of (I) 3-methacryloxypropyltrimethoxysilane, (II) ammonium hydrogen difluoride and (III) 1-methacryloyloxydecane-10-phosphate.

Preferably, these components are used in the aforesaid quantities and as desired with said optional additives.

The invention also relates to the use of the adhesion promoter composition in dentistry and dental technology, in particular the use for the adhesive bonding of metallic or ceramic dental materials, particularly silicate ceramic dental materials with radically curing dental materials, preferably cements, composites and composite-based fixing materials (composite cements), but also filler-free methacrylic acid derivatives and mixtures of methacrylic acid derivatives.

The compositions according to the invention are particularly suitable for use as self-etching primers for silicate ceramics, such as for example feldspar, quartz, leucite or lithium disilicate-based ceramics or other glass-containing ceramics. Compositions which contain a phosphoric acid ester (III) and/or phosphonic acid monomer (IIIa) are also suitable for priming non-silicate ceramics, such as for example yttrium-stabilized zirconium oxide, aluminium oxide, and base metals, such as for example titanium, titanium-containing alloys, chromium-containing, nickel-containing or cobalt-containing dental alloys. After the surface treatment with the primer formulation according to the invention, dental restorations made of the said materials can be securely fixed onto the natural tooth with use of radically curing fixing materials. A good bond is achieved, even after thermal shock, which indicates the high durability of the bond under oral conditions.

The invention also relates to the use of the primer composition according to the invention in dentistry and dental technology, in particular the use as adhesion promoter for adhesive bonding of ceramic dental materials with radically curing dental materials, preferably cements, composites and composite-based fixing materials. The compositions according to the invention are suitable for intraoral use by the dentist (therapeutic use) and extraoral use (non-therapeutic use).

For the treatment with the primer formulations according to the invention, silicate ceramics are cleaned after fabrication. For example, production residues (e.g. moulding or abrasive agent residues) can be removed by the methods usual in dental technology (steam jets, ultrasound bath or water jet). The ceramics are then dried, for example freed from surface-adhering water by means of an air blower. Next, the primer formulation is applied onto the whole adhesion area with a suitable application device (e.g. brush, brush cannula) and left on the ceramic without further agitation, preferably for 15 to 300 sec. Next, excess primer is rinsed off with a water jet and the ceramic dried, e.g. blown dry with an air blower. The further cementation process (application of cement, fitting of the ceramic into the cavity/onto the tooth stump, cement precuring, removal of excess, final cement curing) takes place according to the procedure suitable for the restoration and normal in dental medicine.

For the coating of oxide-ceramic ceramics and base metal restorations with the primer formulations according to the invention, oxide-ceramic and base metal restorations are cleaned after their fabrication. For example, production residues (e.g. moulding or abrasive agent residues) can be removed by the methods usual in dental technology (steam jets, ultrasound bath or water jet). Next the ceramics are dried, for example freed from surface-adhering water with an air blower. Next, the restoration is surface-roughened by the sandblasting method prescribed by the manufacturer of the restoration material. The blasting agent particle size and the blasting pressure are stated in this. The sandblasting process is usually followed by a further cleaning step for removal of the blasting agent residues, for example in an ultrasound bath. After this, the restoration is dried, for example freed from surface-adhering water by means of an air flow. Then primer formulation is applied onto the whole adhesion surface with a suitable applicator device (e.g. brush, brush cannula) and left without further agitation, preferably for 30 to 300 sec on the ceramic or the metal surface. Next, excess primer is rinsed off with a water jet and the restoration dried, e.g. blown dry with an air blower. The further cementation process (application of cement, fitting of the ceramic into the cavity/onto the tooth stump, cement precuring, removal of excess, final cement curing) takes place according to the procedure suitable for the restoration and customary in dental medicine.

The silicate ceramics, oxide ceramics and metal restorations the surface of which is at least partially treated with the primer according to the invention are also subjects of the invention.

The invention is explained in more detail below on the basis of examples.

EXAMPLES

Example 1

Production of Adhesion Promoters (Primers)

The primers A to G stated in the following Table 1 were produced by combining the components and stirring them until homogeneous.

TABLE 1

Composition of primers

| Ingredient | Primer [wt. %] | | | | | | |
|---|---|---|---|---|---|---|---|
| | A | B | C | D | E | F | G |
| Component (1) | | | | | | | |
| 3-methacryloxypropyl-trimethoxysilane[1] | 1.0 | 1.0 | 1.0 | 10.0 | | 3.0 | 3.0 |
| (3-trimethoxysilyl-propyl)methacrylamide[2] | | | | | 1.0 | | |
| Bis(triethoxysilyl)ethane[5] | | | | | | | 0.3 |
| Component (2) | | | | | | | |
| 1-methacryloyloxydecane-10-phosphate[3] | | 1.0 | 1.0 | | | 3.0 | 3.0 |
| 1-methacryloylamidodecane-10-phosphate[4] | | | | | 1.0 | | |
| Component (3) | | | | | | | |
| Tetra-n-butylammonium hydrogen difluoride[5] | 10 | | | | | | |
| Ammonium hydrogen difluoride[6] | | 10 | | | | | |
| Tetra-n-butylammonium dihydrogen trifluoride[7] | | | 10 | 20 | 10 | 10 | 10 |
| (4) Ethanol | 45 | 44 | 44 | 35 | 44 | 41 | 40.7 |
| (5) Water | 44 | 44 | 44 | 35 | 44 | 42 | 42 |
| (6) Additives | | | | | | | |
| Thickener (Methocel 90HG)[8] | | | | | | 1.0 | 1.0 |
| Colorant (Fast Green FCF)[6] | | | | | | | 0.06 |
| Colorant (Coomassie Violet)[6] | | | | | | 0.06 | |

[1] commercially available from Sigma Aldrich
[2] prepared according to Example 1 of EP 2 229 930 A1
[3] prepared according to U.S. Pat. No. 4,612,384 in a yield of 75% and a purity of 95% (determined by HPLC)
[4] prepared according to EP 1 674 066 in a yield of 69% and a purity of 93% (determined by HPLC)
[5] commercially available from ABCR, Karlsruhe, Germany
[6] commercially available from Sigma-Aldrich, Buchs, Switzerland
[7] commercially available from TCI Europe, Zwijndrecht, Belgium
[8] polysaccharide; commercially available from Sigma-Aldrich, Buchs, Switzerland Example 2

Determination of the Adhesion Values on Different Dental Restoration Materials

For the determination of the adhesion values, a pull-off arrangement was used as described in the literature (M. Kern, V. P. Thompson, J. Prost. Dent. 1995 73(3): 240-249; M. Kern, V. P. Thompson, "Eine einfache Versuchsanordnung zur universellen Prüfung des Klebeverbundes im axialen Zugtest" [A simple test arrangement for universal testing of the adhesive bond in the axial tensile test], Dtsch Zahnärztl Z 1993, 48: 769-772).

Materials

The primer formulations A-F according to the invention were compared with the following commercially available ceramic or metal primers:

MBP: Monobond Plus (Ivoclar Vivadent AG, Schaan, Liechtenstein) based on 3-methacryloxypropyltrimethoxysilane, 10-methacryloyloxydecyl dihydrogen phosphate and lipoic acid 2-ethoxycarbonylallyl ester MBS: Monobond-S primer from Ivoclar Vivadent AG, Schaan, Liechtenstein (based on 3-methacryloxypropyltrimethoxysilane)

CP: Clearfil Ceramic primer (Kuraray Europe GmbH, Germany) based on 3-methacryloxypropyltrimethoxysilane and 10-methacryloyloxydecyl dihydrogen phosphate ZP: Z-Prime (BISCO, USA) based on 10-methacryloyloxydecyl dihydrogen phosphate The adhesion promoters according to the invention were tested on the following restoration materials:

E.max: Lithium disilicate ceramic E.max CAD (Ivoclar Vivadent AG, LI),

EMpress: Leucite ceramic Empress (Ivoclar Vivadent AG, Liechtenstein),

ZirCAD: Zirconium oxide ceramic ZirCAD (Ivoclar Vivadent AG, Liechtenstein)

Al-Cube: Aluminium oxide ceramic Al-Cube (Vita, Germany)

Titan: Pure titanium (Tritan, Dentaurum, Germany).

Preparation of the Test Piece Surface

The cube-shaped test pieces were surface-ground with SiC abrasive paper of particle sizes P120 and P400 with water cooling and then polished with P1000.

Etching of Silicate Ceramic with HF for Comparison Measurements

For reference measurements with HF pretreatment, a polished and ultrasound-cleaned lithium disilicate glass ceramic (E.max CAD, Ivoclar Vivadent, Liechtenstein) was contacted for 20 secs without agitation with hydrofluoric acid gel (Ceramic Etch, Ivoclar Vivadent AG, Liechtenstein), rinsed with distilled water and the surface blown dry with oil-free compressed air. In parallel, a leucite-reinforced silicate ceramic (Empress, Ivoclar Vivadent, Liechtenstein) was contacted for 60 secs without agitation with the hydrofluoric acid gel (Ceramic Etch, Ivoclar Vivadent AG, Liechtenstein), rinsed with distilled water and the surface blown dry with oil-free compressed air. The samples were then stored protected from dust until use.

Sandblasting of the Oxide Ceramic and Metallic Samples

The oxide ceramic surfaces zirconium oxide (ZirCAD, Ivoclar Vivadent, Liechtenstein) and aluminium oxide (Al-Cube, Vita, Germany) and pure titanium (Tritan, Dentaurum, Germany) were roughened with 50 μm aluminium oxide blasting agent (Korox 50) at $2.5 \times 10^5$ Pa (2.5 bar) pressure for 15 secs from a distance of ca. 1-2 cm. The samples standing on edge (e.g. adhesion surface vertical with no wall or base contact) were then cleaned for 10 mins in i-propanol in an ultrasound bath. After removal from the i-propanol, the samples were blown dry with compressed air and stored protected from dust until use.

Application of the Primer Formulations not According to the Invention onto Etched or Sandblasted Surfaces For reference measurements with commercially available adhesion promoters, the etched or sandblasted test pieces were treated with the product in accordance with the relevant use directions.

Application of the Primer Formulations According to the Invention onto Polished or Sandblasted Surfaces For the testing of the primers according to the invention, silicate ceramics surface-ground and polished by the preparation process described above, or sandblasted oxide ceramics and metals were contacted with one of the primer formulations according to the invention A-G. For this, the samples were thoroughly coated once with a Microbrush brush impregnated with the primer formulation and the liquid was allowed to act on them for 60 secs. Next, remaining liquid was washed off with tap water and the surface then blown dry with oil-free compressed air.

Measurement of the Tensile Bond Strength

A plexiglas sleeve filled with photopolymerized composite (Multicore Flow, Ivoclar Vivadent AG, Schaan, Liechtenstein) was applied onto the primed surfaces, as described in Dtsch Zahnärztl Z (1993) 48, 769-772. For this, the sleeve was laid on the end to be adhered with one drop of dental cement (Multilink Automix, Ivoclar Vivadent AG, Schaan, Liechtenstein) and pressed onto the ceramic test piece with a pressure apparatus. Then the cement was cured by 2×20 sec irradiation with a polymerization lamp (Type BluePhase G2, Ivoclar Vivadent, Liechtenstein) and the samples stored for 24 hrs at 37° C. in water. After this, the tensile adhesion was determined with the sample holder described in the literature in a universal testing machine (Type Z010, Zwick-Roell, Ulm, Germany).

To simulate prolonged stress, the test pieces were also subjected to thermocycling stress. For this, before measurement of the tensile adhesion, the test pieces were transferred from cold water at 5° C. to warm water at 55° C. and back 10,000 times and left in the water for 60 secs each time.

Results

The results are summarized in Table 2. As the adhesion values in Table 2 show, the primers A, B, C, D, E, F and G according to the invention are characterized by very good bonding to the respective substrate surfaces tested and (where tested) have very good heat resistance comparable to the commercially available products. On silicate ceramic without prior HF etching, adhesion values were obtained which are comparable with or even better than those of the commercial formulations after HF etching. Together with this advantage, with the phosphate-containing formulations C, E and F a bonding to oxide ceramic comparable with the commercial primers MBP and CP was attained. In addition, with formulation C, a good adhesive effect on metals was achieved.

TABLE 2

| Adhesion promoter | Tensile strength [MPa] | Tensile strength after thermal shock [MPa] |
|---|---|---|
| Lithium disilicate ceramic (E. max CAD; Ivoclar Vivadent) | | |
| MBP* | 53.7 ± 7.8 | 44.4 ± 7.0 |
| MBS* | 50.6 ± 15.4 | 46.3 ± 8.9 |
| CP** | 6.1 ± 2.5 | 32.6 ± 10.1 |
| A | 53.0 ± 30.1 | Not determined |
| B | 41.3 ± 4.5 | Not determined |
| C | 48.7 ± 5.9 | 49.1 ± 7.2 |
| D | 49.8 ± 5.1 | 45.9 ± 9.5 |
| E | 45.7 ± 8.1 | Not determined |
| F | 46.1 ± 13.0 | Not determined |
| G | 47.5 ± 14.0 | Not determined |
| Leucite-reinforced silicate ceramic (Empress, Ivoclar Vivadent) | | |
| MBP* | 25.9 ± 8.4 | 32.2 ± 13.6 |
| MBS* | 31.1 ± 11.4 | Not determined |
| C | 43.9 ± 3.2 | 53.9 ± 3.8 |
| Zirconium oxide ceramic (ZirCAD, Ivoclar Vivadent) | | |
| MBP*** | 49.3 ± 5.2 | 47.1 ± 6.2 |
| CP*** | 40.5 ± 5.8 | Not determined |
| ZP*** | 38.0 ± 13.4 | Not determined |
| C | 43.3 ± 4.9 | 53.9 ± 3.8 |
| E | 34.1 ± 7.1 | Not determined |
| F | 39.4 ± 6.0 | Not determined |
| Aluminium oxide ceramic (Al-Cube, VITA) | | |
| MBP*** | 33.5 ± 13.2 | 11.5 ± 10.9 |
| C | 25.7 ± 4.6 | 10.8 ± 5.8 |
| Titanium (Tritan, 99.5% titanium, Dentaurum) | | |
| MBP*** | 19.6 ± 5.3 | 5.7 ± 3.4 |
| C | 17.9 ± 10.6 | 10.4 ± 8.2 |

*Comparative example, sample pre-etched with HF
**Comparative example, with fixing cement Panavia F2.0 (Kuraray Europe, Germany)
***Comparative example Example 3

Investigation of the Release of HF Using $^{19}$F-NMR Spectroscopy

The stability of the polyhydrogen fluoride salts towards hydrolytic decomposition and release of HF was tested by $^{19}$F-NMR spectroscopy on homogeneous solutions in H$_2$O/ethanol (50/50%)+d$_6$-ethanol. The spectroscopic studies were performed on solutions of the salts NBu$_4$HF$_2$ and NBu$_4$H$_2$F$_3$. In addition, the primer formulations A (containing NBu$_4$HF$_2$, alkoxysilane monomer MPTMS) and C (containing NBu$_4$H$_2$F$_3$, alkoxysilane monomer MPTMS and phosphoric acid ester monomer MDP) were tested. Some of the samples (as noted in Table 3) were stored before the measurement in order to be able to definitely exclude gradual HF release due to slow hydrolysis. On primer C, the spectroscopic testing was carried out before, during and after 8-week stress storage at 50° C. for accelerated aging.

The absence of free hydrofluoric acid HF in the primer formulations was demonstrated by $^{19}$F-NMR spectroscopy through the absence of the corresponding singlet signal at −162.9 to −165.8 ppm. This signal is also not detectable after 8-week stress storage at 50° C., so that the absence of HF can be regarded as a stable property of the primer formulations according to the invention. The NMR spectra thus confirm the stability of the primer formulations containing polyhydrogen fluoride salts against hydrolytic decomposition and release of HF.

Figure 1:
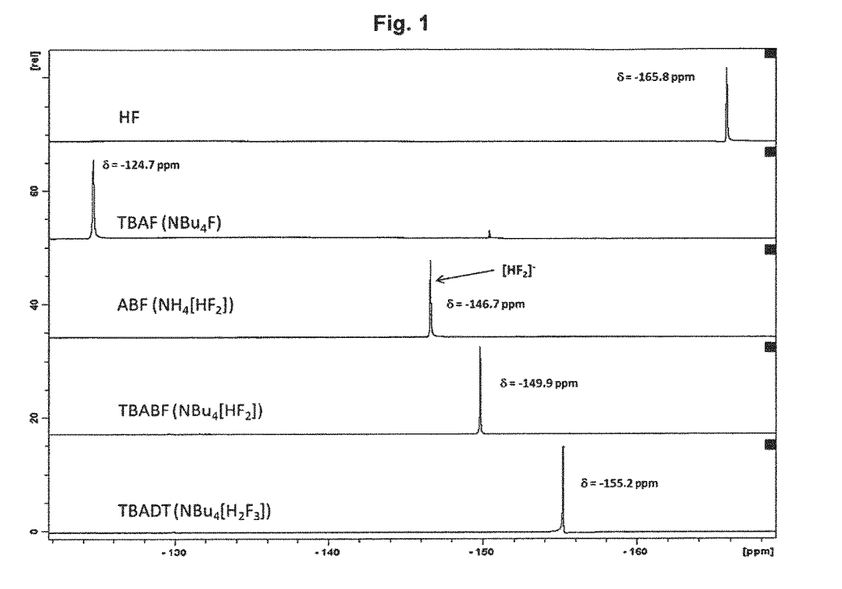
FIG. 1 shows 19F-NMR spectra of various fluoride compounds (hydrogen fluoride, HF; tetrabutylammonium fluoride, TBAF, ammonium bifluoride, ABF; tetrabutylammonium hydrogen difluoride TBABF and tetrabutylammonium dihydrogen trifluoride, TBADT).

FIG. 1 shows $^{19}$F-NMR spectra of various fluoride compounds (hydrogen fluoride, HF; tetrabutylammonium fluoride, TBAF, ammonium bifluoride, ABF; tetrabutylammonium hydrogen difluoride TBABF and tetrabutylammonium dihydrogen trifluoride, TBADT). Measurement as homogenous solutions in H$_2$O/ethanol (50/50%)+d$_6$-ethanol.

Figure 2:
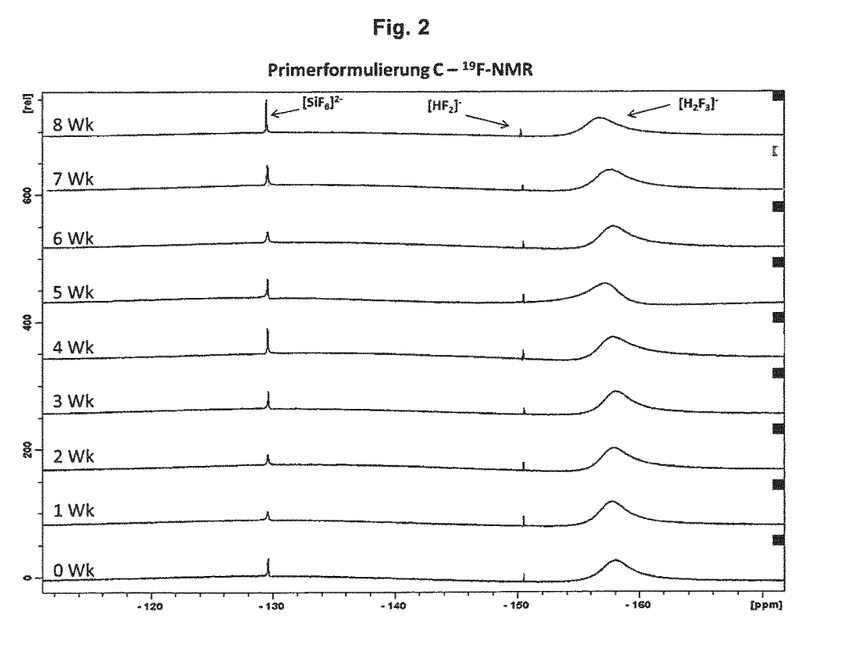
FIG. 2 shows the 19F-NMR spectrum of the primer formulation C during storage at 50° C. for 8 weeks.
Figure 3:
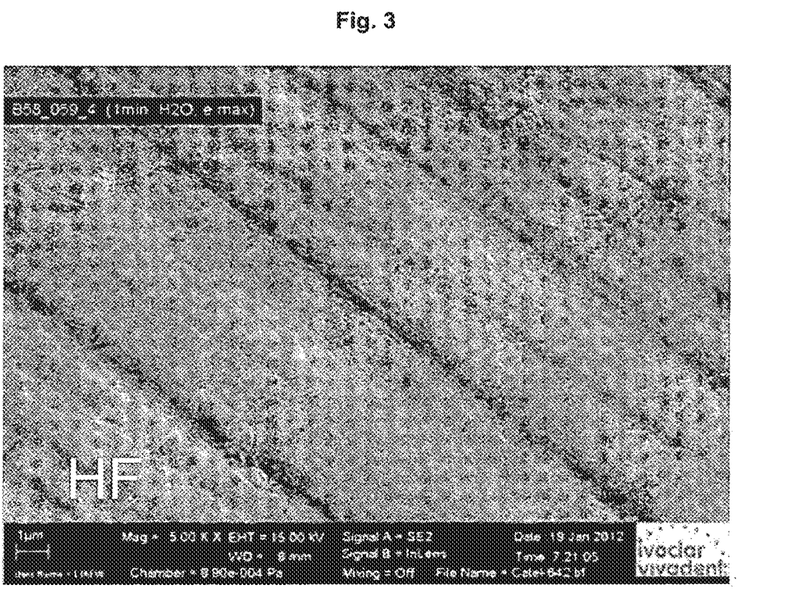
FIG. 3 shows the wet-chemical erosion achieved on lithium disilicate ceramic (E.max, Ivoclar Vivadent AG) due to hydrofluoric acid, HF (0.325 M; $H_2O$/ethanol 50/50 vol. %) after 1 minute agitation-free contact and rinsing off with water.

FIG. 2 shows the $^{19}$F-NMR spectrum of the primer formulation C during storage at 50° C. for 8 weeks. Measurement as homogeneous solutions in H$_2$O/ethanol (50/50%)+d$_6$-ethanol.

to hydrofluoric acid, HF (0.325 M; H$_2$O/ethanol 50/50 vol. %) after 1 minute agitation-free contact and rinsing off with water.

Figure 4:
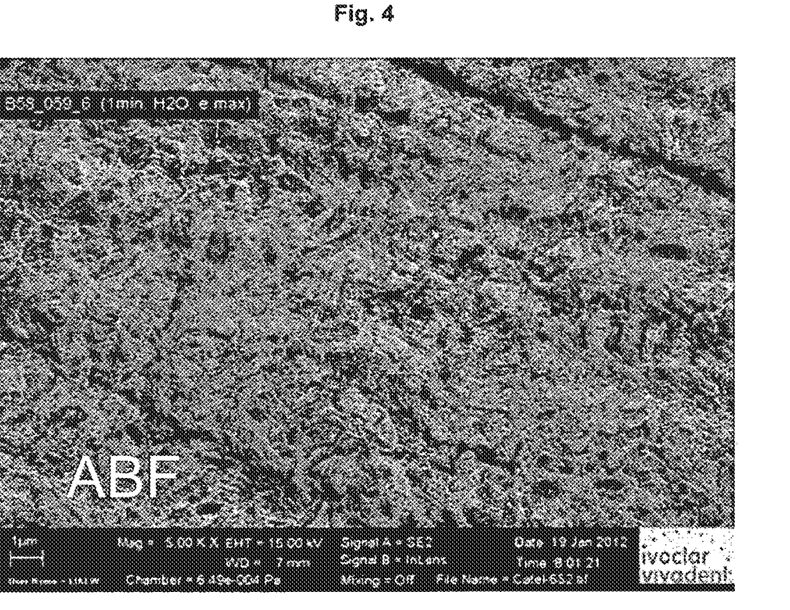
FIG. 4 shows the wet-chemical erosion achieved on lithium disilicate ceramic (E.max, Ivoclar Vivadent AG) due to ammonium bifluoride, $NH_5F_2$ ABF (0.325 M; $H_2O$/ethanol 50/50 vol. %) after 1 minute agitation-free contact and rinsing off with water.

FIG. 4 shows the wet-chemical erosion achieved on lithium disilicate ceramic (E.max, Ivoclar Vivadent AG) due to ammonium bifluoride, NH$_5$F$_2$, ABF (0.325 M; H$_2$O/ethanol 50/50 vol. %) after 1 minute agitation-free contact and rinsing off with water.

TABLE 3

| Primer | Fluoride source | Sample age on measurement | Monomer [wt. %] | Solvent [wt. %] | δ($^{19}$F) ppm (%) |
|---|---|---|---|---|---|
| — | HF (0.65%, 0.325M) | freshly prepared | — | H$_2$O/EtOH (50/50%) | −165.8 (singlet) |
| — | NBu$_4$HF$_2$ (10%, 0.356M) | freshly prepared | — | H$_2$O/EtOH (45/45%) | −147.6 (broad) |
| — | NBu$_4$HF$_2$ (9.1%, 0.325M) | 1 week at room temperature | — | H$_2$O/EtOH | −149.9 (broad) −129.6 (multi) |
| — | NBu$_4$H$_2$F$_3$ (19.5%, 0.65M) | freshly prepared | — | H$_2$O/EtOH (40/40%) | −156.6 (broad) −129.9 (multi) |
| — | NBu$_4$H$_2$F$_3$ (10%, 0.325M) | freshly prepared | — | H$_2$O/EtOH (45/45%) | −155.2 (broad) −130.0 (multi) |
| — | NBu$_4$H$_2$F$_3$ (5%, 0.167M) | freshly prepared | — | H$_2$O/EtOH (47.5/47.5%) | −154.5 (broad) −130.0 (multi) |
| — | NBu$_4$H$_2$F$_3$ (20%, 0.65M) | 4 weeks at room temperature | MPTMS (10%) | H$_2$O/EtOH (35/35%) | −130.4 (broad) −117.1 (multi) |
| A | NBu$_4$HF$_2$ (10%, 0.356M) | freshly prepared | MPTMS (1%) | H$_2$O/EtOH (44.5/44.5%) | −145.6 (broad) −129.6 (multi) −116.7 (multi) |
| C | NBu$_4$H$_2$F$_3$ (10%, 0.325M) | freshly prepared | MPTMS (1%) MDP (1%) | H$_2$O/EtOH (44.5/44.5%) | −145.6 (broad) −129.6 (multi) −116.7 (multi) |
| C | NBu$_4$H$_2$F$_3$ (10%, 0.325M) | 8 weeks at 50° C. | MPTMS (1%) MDP (1%) | H$_2$O/EtOH (44.5/44.5%) | −145.6 (broad) −129.6 (multi) −116.7 (multi) |

Example 4

Scanning Electron Microscopy (SEM) of Wet-Chemical Eroded Silicate Ceramics

Figure 5:
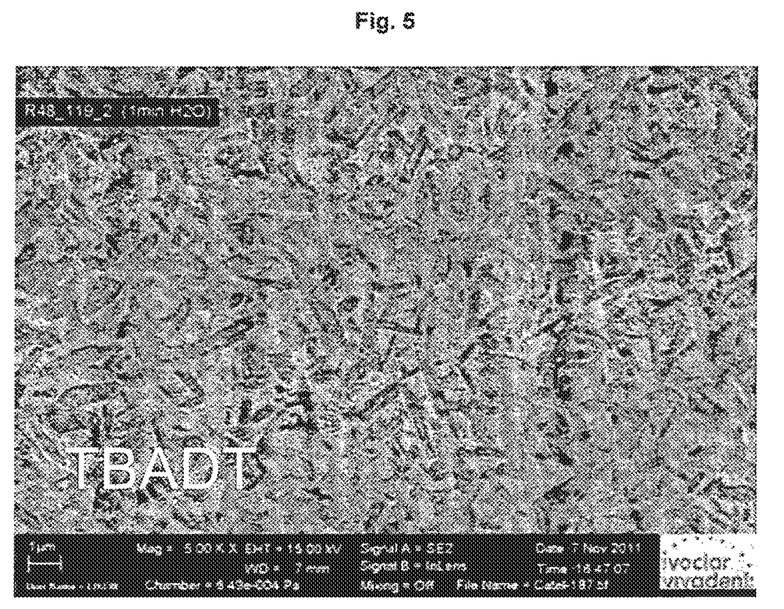
FIG. 5 shows the wet-chemical erosion achieved on lithium disilicate ceramic (E.max, Ivoclar Vivadent AG) due to tetrabutylammonium dihydrogen trifluoride, $NBu_4H_2F_3$, TBADT (0.325 M; $H_2O$/ethanol 50/50 vol. %) after 1 minute agitation-free contact and rinsing off with water.

The capacity of the polyhydrogen fluoride salts for wet-chemical erosion of silicate ceramics was demonstrated by SEM analysis (see FIG. 3-5). The pictures confirmed the desired formation of micromechanical retention sites on the ceramic with the exposure times of 1 minute without agitation usual in dental medicine. Surprisingly, the formation of micromechanical retention sites with polyhydrogen fluoride salt solutions was in fact more pronounced than with an equimolar HF solution in the same solvent (H$_2$O/ethanol, 0.325 M), which is a further advantage of the primer formulations according to the invention.

FIG. 3 shows the wet-chemical erosion achieved on lithium disilicate ceramic (E.max, Ivoclar Vivadent AG) due FIG. 5 shows the wet-chemical erosion achieved on lithium disilicate ceramic (E.max, Ivoclar Vivadent AG) due to tetrabutylammonium dihydrogen trifluoride, NBu$_4$H$_2$F$_3$, TBADT (0.325 M; H$_2$O/ethanol 50/50 vol. %) after 1 minute agitation-free contact and rinsing off with water.

Figure 6:
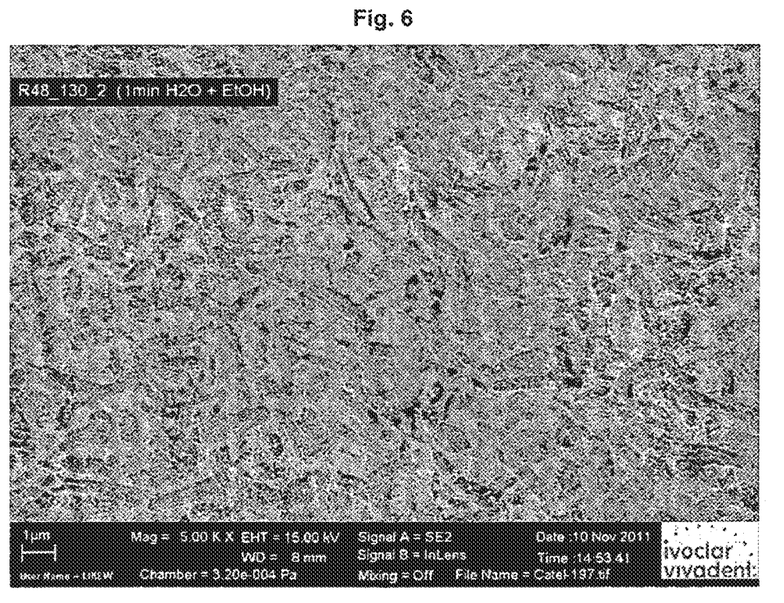
FIG. 6 shows the wet-chemical erosion achieved on lithium disilicate ceramic (E.max, Ivoclar Vivadent AG) due to primer formulation C (containing tetrabutylammonium dihydrogen trifluoride, $NBu_4H_2F$, TBADT; 0.325 M; $H_2O$/ethanol 50/50 vol. %) after 1 minute agitation-free contact and rinsing off with water.
Figure 7:
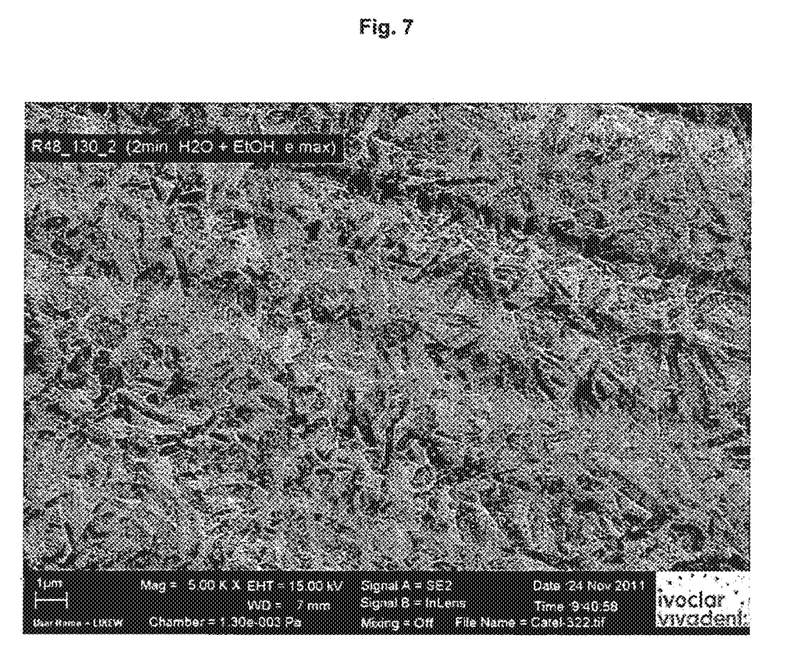
FIG. 7 shows the wet-chemical erosion achieved on lithium disilicate ceramic (E.max, Ivoclar Vivadent AG) due to primer formulation C (containing tetrabutylammonium dihydrogen trifluoride, $NBu_4H_2F_3$, TBADT; 0.325 M; $H_2O$/ethanol 50/50 vol. %) after 2 minutes agitation-free contact and rinsing off with water.

With primer formulation C, the effect of a doubled exposure time on lithium disilicate ceramics was investigated by SEM analysis (FIGS. 6 and 7). The etching pattern after 1 minute contact time is not different from that after 2 minutes contact time. The whitish deposits of liberated lithium disilicate crystallites characteristic of over-etched lithium disilicate ceramics could not be observed on the ceramic surface, nor are crystallites not bound into the amorphous phase visible in the SEM pictures. Such loose bounded crystallites form predetermined breaking points in the adhesive bond between ceramic and fixing material and through their presence can considerably weaken the adhesive action. It is therefore advantageous for the user to be able reliably to avoid the over-etching of a ceramic. The low tendency of the primer formulations to over-etching of the ceramic on unintentionally prolonged contact is thus a considerable advantage of the primer formulation according to the invention compared to the standard HF etching.

FIG. 6 shows the wet-chemical erosion achieved on lithium disilicate ceramic (E.max, Ivoclar Vivadent AG) due to primer formulation C (containing tetrabutylammonium dihydrogen trifluoride, $NBu_4H_2F_3$, TBADT; 0.325 M; $H_2O$/ethanol 50/50 vol. %) after 1 minute agitation-free contact and rinsing off with water.

FIG. 7 shows the wet-chemical erosion achieved on lithium disilicate ceramic (E.max, Ivoclar Vivadent AG) due to primer formulation C (containing tetrabutylammonium dihydrogen trifluoride, $NBu_4H_2F_3$, TBADT; 0.325 M; $H_2O$/ethanol 50/50 vol. %) after 2 minutes agitation-free contact and rinsing off with water.

The invention claimed is:
1. Primer formulation comprising
   (1) at least one alkoxysilane monomer of the general formula (I)

$$R^1{}_n Si(OR^2)_{4-n} \quad (I),$$

in which
   $R^1$ stands for an organic residue which contains at least one ethylenically unsaturated, polymerizable group,
   $R^2$ stands for a $C_1$-$C_8$ alkylorganic residue and
   n is 1, 2 or 3,
   wherein the residues $R^1$ and $R^2$ can each be the same or different;
   (2) at least one polyhydrogen fluoride salt of the general formula (II)

$$(R^9)^+(H_{x-1}F_x)^-{}_z \quad (II),$$

in which
   $R^9$ stands for a metal cation from the series of the alkali, alkaline earth or transition metals or for an ammonium ion of the formula $(R^5)(R^6)(R^7)(R^8)N^+$, in which $R^5$, $R^6$, $R^7$ and $R^8$ each independently of each other stand for H or $C_1$- to $C_{26}$ alkyl, $C_3$ to $C_{26}$ alkenyl or $C_6$-$C_{26}$ aryl residues, wherein $R^5$, $R^6$, $R^7$ and $R^8$ can be the same or different, and wherein two of these residues can be bound together to form a heterocycle together with the nitrogen atom and wherein three of the residues and the nitrogen atom can together form a pyridinium ion,
   x is an integer from 2 to 5,
   z corresponds to the valence of the cationic residue $R^9$,
   (3) organic solvent, and
   (4) water,
wherein the primer formulation is for use in dentistry.

2. Primer formulation according to claim 1, in which at least one or all variables have one of the following meanings:
Formula (I):
   $R^1$=a residue with the following formula:

$$R^{1a}-CH=\underset{R^{1b}}{C}-X-R^{1c}-$$

in which
   $R^{1a}$=H or phenyl;
   $R^{1b}$=H or methyl;
   $R^{1c}$ is absent or is $C_1$-$C_{16}$ alkyl;
   X is absent or is —CO—O— or —CO—NH—, wherein X is absent when $R^{1c}$ is absent;
   $R^2$=H or $C_1$ to $C_2$ alkyl and
   n=1 or 2,
   wherein the residues $R^1$ and $R^2$ can each be the same or different;
Formula (II)
   x=an integer from 2 to 4,
   z=1
   $R^9$=an ammonium ion of the formula $(R^5)(R^6)(R^7)(R^8)N^+$, wherein $R^5$, $R^6$, $R^7$ and $R^8$ independently of each other mean H, $C_1$-$C_4$ alkyl.

3. Primer formulation according to claim 2, wherein in Formula (I):
   $R^{1a}$=H;
   $R^{1b}$=methyl;
   $R^{1c}$=$C_1$-$C_3$ alkyl;
   X=—CO—O— or —CO—NH—
   $R^1$ and $R^2$ are the same;
in Formula (II)
   x=3,
   $R^5$, $R^6$, $R^7$ and $R^8$ are the same.

4. Primer formulation according to claim 2, wherein in Formula (II)
   $R^5$=$R^6$=$R^7$=$R^8$=butyl.

5. Primer formulation according to claim 1, which as solvent contains an alcohol, a ketone, an ester or a mixture thereof.

6. Primer formulation according to claim 5, which comprises an alcohol which is selected from one or more of methanol, ethanol, n-propanol, propanol, and t-butanol.

7. Primer formulation according to claim 5, which comprises a ketone which is selected from one or more of acetone, methyl ethyl ketone.

8. Primer formulation according to claim 5, which comprises an ester which is ethyl acetate.

9. Primer formulation according to claim 1, which contains no free hydrofluoric acid (HF).

10. Primer formulation according to claim 1, which additionally contains at least one phosphoric or pyrophosphoric acid ester monomer of Formula (III):

$$O=P(OR^3)_m(OR^4)_{3-m} \quad (III),$$

in which
   $R^3$ stands for an organic residue which contains at least one ethylenically unsaturated, polymerizable group,
   $R^4$ stands for H, $SiR_3$, $P(=O)(OR^{14})_2$ or $C_1$ to $C_{16}$ alkyl, wherein $R^{14}$ stands for H, $SiR'_3$ or $C_1$ to $C_{16}$ alkyl and wherein R and R' are each independently of each other $C_1$ to $C_4$ alkyl, and
   m is 1 or 2,
wherein the residues $R^3$ and $R^4$ can each be the same or different, and/or
at least one phosphoric or polyphosphoric acid monomer of the general formula (IIIa):

$$R^{11}[P(=O)(OR^{10})_2]_n \quad (IIIa)$$

in which
   $R^{11}$ stands for an organic residue which contains at least one ethylenically unsaturated, polymerizable group,
   $R^{10}$ stands for a residue selected from H, $SiR''_3$ or $C_1$ to $C_{16}$ alkyl, wherein R" is $C_1$ to $C_4$ alkyl, and
   n is 1, 2, 3 or 4.

11. Primer formulation according to claim 1, which additionally contains at least one additive, which is selected from wetting agents, detergents, non-ionic, anionic and/or cationic surfactants, antifoaming agents, stabilizers, antimicrobial additives, fragrances, colorants, preservatives, polymeric thickeners, thixotropic agents and rheology modifiers.

12. Primer formulation according to claim 11, comprising a detergent selected from one or more of non-ionic, anionic and/or cationic surfactants.

13. Primer formulation according to claim 11, comprising a polymeric thickener selected from one or more of polyvinyl compounds, polymethacrylates, polyacrylates, polyethers, polyamines, polysilicates, and polysaccharides.

14. Primer formulation according to claim 1, which additionally contains an alkoxysilane of the general formula (Ia), $$(OR^{13})_3SiR^{12}Si(OR^{13})_3 \quad \text{(Ia),}$$

in which
$R^{12}$ stands for $C_1$-$C_{12}$ alkylene, $C_1$-$C_{12}$ heteroalkylene or $C_6$-$C_{12}$ arylene,
$R^{13}$ each independently stands for H or $C_1$ to $C_8$ alkyl
wherein the residues $R^{13}$ can each be the same or different.

15. Primer formulation according to claim 1, which contains
(1) 0.05 to 25.0 wt. % of alkoxysilane monomer (I);
(2) 1.0 to 25.0 wt. % of polyhydrogen fluoride salt (II);
(3) 25 to 98.5 wt. % of organic solvent;
(4) 25 to 98.5 wt. % water;
each based on the total weight of the composition.

16. Primer formulation according to claim 15, which additionally contains
0.005 to 2.5 wt. % of the alkoxysilane (Ia); and/or
0.05 to 25.0 wt. % of phosphoric acid ester monomer (III) and/or
0.05 to 25.0 wt. % of phosphonic acid monomer (IIIa); and/or
0.001 to 10% of additives,
each based on the total weight of the composition.

17. Primer formulation according to claim 15, which contains
(1) 0.2 to 10.0 wt. % of alkoxysilane monomer (I);
(2) 2.0 to 15.0 wt. % polyhydrogen fluoride salt (II);
(3) 35 to 75 wt. % of organic solvent;
(4) 25 to 98.5 wt. % water;
each based on the total weight of the composition.

18. Primer formulation according to claim 15, which contains
(1) 0.5 to 5.0 wt. % of alkoxysilane monomer (I);
(2) 5.0 to 10.0 wt. % of polyhydrogen fluoride salt (II);
(3) 45 to 55 wt. % of organic solvent;
(4) 40 to 75 wt. % water;
each based on the total weight of the composition.

19. Primer formulation according to claim 15, which additionally contains
0.02 to 1.0 wt. % of the alkoxysilane (Ia); and/or
0.2 to 10.0 wt. % of phosphoric acid ester monomer (III) and/or
0.2 to 10.0 wt. % of phosphonic acid monomer (IIIa); and/or
0.1 to 7.5% of additives,
each based on the total weight of the composition.

20. Primer formulation according to claim 15, which additionally contains
0.05 to 0.5 wt. % of the alkoxysilane (Ia); and/or
0.5 to 5.0 wt. % of phosphoric acid ester monomer (III) and/or
0.5 to 5.0 wt. % of phosphonic acid monomer (IIIa); and/or
1.0 to 5% of additives,
each based on the total weight of the composition.

21. Primer formulation according to claim 1, wherein x is an integer from 2 to to 4.

22. Primer formulation according to claim 1, wherein x is 3.

23. Method of use of a primer formulation according to claim 1 comprising applying the primer formulation as a surface treatment of metallic or ceramic dental restorations or dental materials.

24. Method of use according to claim 23 wherein the dental restoration or dental material is based on silicate ceramic.

25. Method of use of a primer formulation according to claim 1 comprising applying the primer formulation as an adhesion promoter.

26. Dental restoration, characterized in that at least a part of its surface is treated with a primer formulation according to claim 1.

27. Dental restoration according to claim 26, which has a surface of silicate ceramic, feldspar, quartz, leucite or lithium disilicate-based ceramic.

\* \* \* \* \*